(12) United States Patent
Yoda et al.

(10) Patent No.: US 7,933,376 B2
(45) Date of Patent: Apr. 26, 2011

(54) X-RAY CT SYSTEM AND A METHOD FOR CREATING A SCANNING PLAN

(75) Inventors: Takahiro Yoda, Otawara (JP); Takashi Tanaka, Nasushiobara (JP); Shinya Kawanabe, Nasushiobara (JP); Hiroyuki Onuki, Nasushiobara (JP); Hiromitsu Seto, Otawara (JP); Masao Yamahana, Nasushiobara (JP); Katsuhiko Ishida, Nasushiobara (JP); Naoki Yamashita, Nasushiobara (JP); Yuuki Mori, Sapporo (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 104 days.

(21) Appl. No.: 12/329,835

(22) Filed: Dec. 8, 2008

(65) Prior Publication Data
US 2009/0147909 A1 Jun. 11, 2009

(30) Foreign Application Priority Data
Dec. 11, 2007 (JP) ................. 2007-319285

(51) Int. Cl.
G01N 23/083 (2006.01)
H05G 1/00 (2006.01)
A61B 6/08 (2006.01)

(52) U.S. Cl. .......................................... 378/4; 378/205

(58) Field of Classification Search ............... 378/4–20, 378/91, 95, 98.11, 98.12, 109, 110, 204, 378/205, 210, 901; 382/151
See application file for complete search history.

(56) References Cited

U.S. PATENT DOCUMENTS

| | | | | |
|---|---|---|---|---|
| 6,385,280 | B1 * | 5/2002 | Bittl et al. ................ | 378/16 |
| 7,012,603 | B2 * | 3/2006 | Chen et al. ............... | 345/419 |
| 7,113,653 | B2 * | 9/2006 | Kuroiwa et al. .......... | 382/294 |
| 7,653,264 | B2 * | 1/2010 | Hero et al. ................ | 382/294 |
| 7,697,663 | B2 * | 4/2010 | Gertner .................... | 378/65 |
| 2004/0013293 | A1 * | 1/2004 | Klingenbeck-Regn ... | 382/131 |
| 2005/0053200 | A1 * | 3/2005 | Sukovic et al. ........... | 378/210 |
| 2005/0203372 | A1 * | 9/2005 | Janssen et al. ............ | 600/407 |
| 2006/0002631 | A1 * | 1/2006 | Fu et al. ................... | 382/294 |
| 2008/0292048 | A1 * | 11/2008 | Haras et al. .............. | 378/20 |

FOREIGN PATENT DOCUMENTS

| | | |
|---|---|---|
| JP | 2004-298247 | 10/2004 |
| JP | 2006-167042 | 6/2006 |

* cited by examiner

*Primary Examiner* — Edward J Glick
*Assistant Examiner* — Anastasia Midkiff
(74) *Attorney, Agent, or Firm* — Oblon, Spivak, McClelland, Maier & Neustadt, L.L.P.

(57) ABSTRACT

A condition on the attribute of an image for generating multi-frame image data containing a plurality of frames of images per file from image data is stored beforehand. When image data is received, multi-frame image data is generated from the received image data based on incidental information contained in the image data and the condition stored beforehand. Then, the generated multi-frame image data is archived. When a request for an image is made by a certain terminal, an application functioning on the terminal is identified, and multi-frame image data appropriate for the application is sent from among the generated multi-frame image data.

17 Claims, 19 Drawing Sheets

FIG. 5

| SUBJECT INFORMATION | CAPTURING DATE INFORMATION | SITE INFORMATION | ARCHIVE DESTINATION INFORMATION |
|---|---|---|---|
| Taro | 99/01/07 | CHEST | c:¥pict¥Taro¥··· |
| ··· | ··· | ··· | ··· |

X-RAY CT SYSTEM AND A METHOD FOR CREATING A SCANNING PLAN

BACKGROUND OF THE INVENTION

1. Field of the Invention

The present invention relates to a technology of creating a scanning plan for an X-ray CT system.

2. Description of the Related Art

An X-ray CT system may irradiate a subject with X-rays from a plurality of directions and process the respective X-rays transmitted through the subject as projection data, thereby reconstructing the inside of the subject as an image. In order to acquire and reconstruct an image of the inside of a subject with this X-ray CT system, there is a need to create a scanning plan beforehand. A scanning plan contains various kinds of setting contents, for example, scanning conditions such as a scanning region irradiated with an X-ray, a tube voltage and tube current of an X-ray tube and a time to irradiate with an X-ray, and scanning methods such as dynamic scanning and helical scanning. The scanning plan data containing such setting contents is outputted to a controller, whereby driving of the X-ray CT system is controlled.

Conventionally, setting of the scanning region and the tube current in the scanning plan is done based on a scout image as shown in, for example, Japanese Unexamined Patent Application Publication No. 2004-298247. A scout image is an X-ray transmission image of a subject to be captured. The X-ray CT system captures scout images from two orthogonal directions, i.e., from the front and side of a subject by dual scanogram imaging beforehand, and causes a display device to display these scout images. An operator inputs the settings of the scanning region and the tube current based on the scout images via a graphical user interface (GUI).

For example, when inputting the scanning region, the operator operates a mouse, a trackball, etc., to draw a desired region as the scanning region on the scout image. A frame body surrounding the region is displayed on the scout image as position mark information that represents the scanning region.

Further, the X-ray CT system acquires the pixel value of the scout image and, from that pixel value, calculates the tube current at a position of the X-ray tube corresponding to a view angle orthogonal to the scout image. View angles other than the view angle orthogonal to the scout image are estimated on the basis of the tube currents obtained based on the scout images from the two orthogonal directions on the assumption that the subject is an ellipse.

Thus, according to the technique of creating a scanning plan with a scout image, the operator needs to estimate the position, range and shape of a subject to be captured such as an organ on the basis of an X-ray transmission image of a single plane or X-ray transmission images of two orthogonal planes, and input a scanning region. It is required that the scanning region accurately includes the subject to be captured in order to obtain a high diagnostic effect, and it is important that the other regions are excluded in order to reduce unnecessary exposure. However, by the conventional method based on the estimation of the operator, it is difficult to precisely set the scanning region.

Further, as described above, in a case where the tube current is calculated at each position on the body axis and at each view angle from an X-ray transmission image of a single plane or X-ray transmission images of two orthogonal planes, the view angles other than the view angle orthogonal to the X-ray transmission image must be approximate values based on values calculated from the X-ray transmission image.

SUMMARY OF THE INVENTION

The present invention is devised in view of the problems as described above, and an object of the present invention is to provide an X-ray CT system capable of creating a scanning plan with high precision and also provide a method for creating a scanning plan for the system.

In a first aspect of the present invention, an X-ray CT system that irradiates with an X-ray to capture a cross-sectional image of a subject placed on a bed, is provided with: an image storage configured to store a previous image containing previous three-dimensional volume data of the subject; a capturing part including an X-ray tube irradiating with an X-ray, and configured to capture an X-ray transmission image of the subject; a measuring part configured to measure an amount of displacement between images of the subject shown in the previous image and the X-ray transmission image; an inputting part for setting a scanning region; a display controller configured to control so as to display position mark information representing the scanning region on an image based on the three-dimensional volume data in response to an input to the inputting part; and a scanning controller configured to move relative positions of the X-ray tube and the subject by using the amount of displacement so that the scanning region set on the image based on the three-dimensional volume data is captured, and to control the capturing part to capture the cross-sectional image.

Further, in a second aspect of the present invention, the X-ray CT system is further provided with: a tube current calculator configured to calculate a tube current at each capturing position on the basis of an inputted image SD value and the three-dimensional volume data, and link the each position with the tube current; and a correcting part configured to correct the position by the amount of displacement in the link, and when the X-ray tube reaches the corrected position, a tube current linked with the corrected position is applied to the X-ray tube.

Further, in a third aspect of the present invention, a method for creating a scanning plan for an X-ray CT system having a capturing part that includes an X-ray tube irradiating with an X-ray and that is configured to capture a cross-sectional image of a subject placed on a bed, and an inputting part for setting a scanning region of the subject, includes: storing a previous image containing previous three-dimensional volume data of the subject; capturing an X-ray transmission image of the subject by the capturing part; measuring the amount of displacement in image of the subject shown in the previous image and the X-ray transmission image; displaying position mark information showing the scanning region in response to an input to the inputting part, on an image based on the three-dimensional volume data; and moving relative positions of the X-ray tube and the subject by using the amount of displacement so that the scanning region set on the image based on the three-dimensional volume data is captured, and controlling the capturing part to capture the cross-sectional image.

Further, in a fourth aspect of the present invention, in the scanning plan creating method: a tube current at each capturing position is calculated based on an inputted image SD value and the three-dimensional volume data, and the each position is linked with the tube current; in the link, the position is corrected by the amount of displacement; and when the X-ray tube reaches the corrected position, a tube current linked with the corrected position is applied to the X-ray tube.

According to the first and third aspects, by measuring the amount of displacement of a subject from a previous image and an X-ray transmission image captured for actual scan this time and using for correction, it becomes possible to input a scanning region by using an image based on previous three-dimensional volume data of the subject, and accurately present a capturing site such as an organ to the operator as compared with a case of using a scanning plan based on an X-ray transmission image. Accordingly, it is no longer necessary for the operator to estimate the spatial position, and it is possible to determine the scanning region with high precision.

Further, according to the second and fourth aspects of the present invention, by referring to the three-dimensional volume data, it is also possible to precisely set a tube current for each view angle not orthogonal to a scout image, without requiring estimation, and it becomes possible to capture a favorable image.

BRIEF DESCRIPTION OF THE DRAWINGS

FIG. 5 shows the data structure of a database for searching a previous image.

DETAILED DESCRIPTION OF THE PREFERRED EMBODIMENT

Below, preferred embodiments of an X-ray CT system and a method for creating a scanning plan for the system according to the present invention will be specifically described with reference to the drawings.

Figure 1:
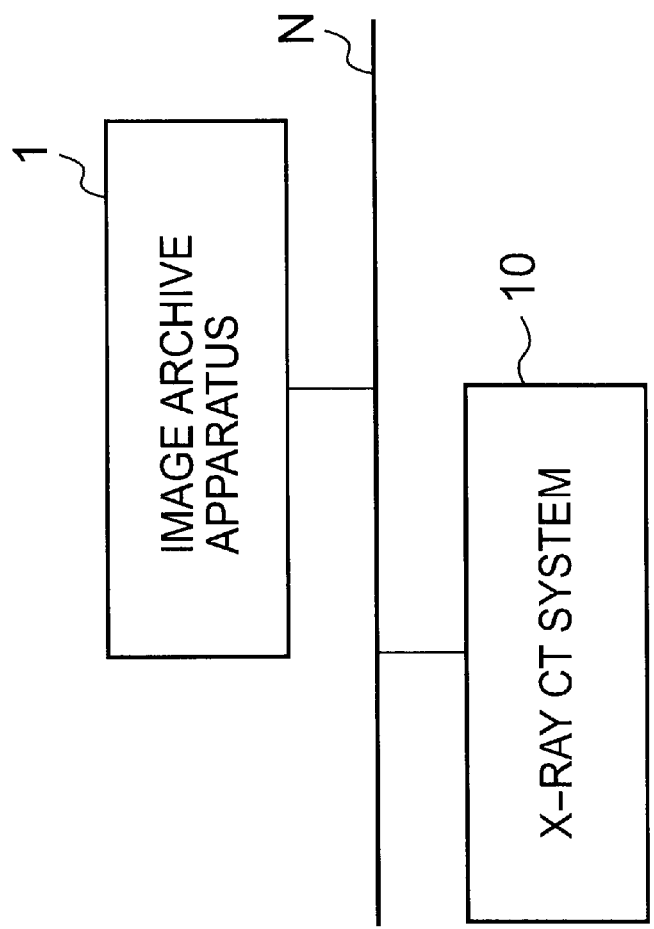
FIG. 1 shows an in-hospital network that contains an X-ray CT system.

FIG. 1 is a diagram showing an in-hospital network containing an X-ray CT system 10 that implements a method for creating a scanning plan according to the present embodiment. To an in-hospital network N, an image archive apparatus 1 and the X-ray CT system 10 are connected. The image archive apparatus 1 archives previous images of a subject P captured with the X-ray CT system 10. This image archive apparatus 1 may be mounted on the X-ray CT system 10 and functionally connected therein electrically or by execution of a program of a computer.

The previous images archived by the image archive apparatus 1 are X-ray transmission images and three-dimensional volume data. An X-ray transmission image is a transmission image captured beforehand in pre-scan by an X-ray for creation of a scanning plan, and is also called a scout image. Three-dimensional volume data is volume data captured and obtained three-dimensionally during actual scan in accordance with a scanning plan. The previous image may be, instead of the three-dimensional volume data, only a three-dimensional image obtained by executing a rendering process on the volume data or an multiplanar reformation (MPR) image.

The X-ray CT system 10 creates a scanning plan with reference to images based on previous three-dimensional volume data read out from the image archive apparatus 1. The images based on the three-dimensional volume data are three-dimensional images generated by volume rendering and MPR images of cross-sections of arbitrary sites.

To be specific, with reference to the images based on the previous three-dimensional volume data, a scanning region to become an X-ray irradiation region in actual scan can be inputted. Moreover, with reference to the previous three-dimensional volume data, a tube current at each view angle is set. Specifically, the X-ray CT system 10 displays an image based on the previous three-dimensional volume data read out from the image archive apparatus 1 in order to create a scanning plan. The operator refers to the image based on the previous three-dimensional volume data, and inputs the range of a scanning region irradiated with an X-ray during actual scan in relationship with the subject P shown in the image based on the previous three-dimensional volume data. For example, in a case where capture of the left lung field of the subject P is aimed, the range of the scanning region is defined so as to encompass the left lung field of the subject P shown in the image based on the three-dimensional volume data. The range of the scanning region to be inputted is a position and a spread with reference to the position.

In actual scan, a bed for placing the subject is held at one end of the scanning region or backward by an extra width from the position, and then moved to the other end of the scanning region, whereby the set scanning region is irradiated with an X-ray. Accordingly, by calculating a bed position from the coordinate position of an image reflecting the present placement state of the subject P on the bed, the scanning region is eventually represented with information showing the bed position. The on-bed placement state includes the placement positions of the subject P in the long-side direction and the short-side direction of the bed, and the height of the bed.

There is a difference in on-bed placement state of the subject between the time of capture of the previous three-dimensional volume data and the present time. Therefore, the X-ray CT system 10 measures the amount of displacement in image of the subject P between the time of capture of the previous image and the time of capture of the scout image this time, from the previous image and the scout image captured in pre-scan this time. Then, the position of the scanning region inputted in relationship with the image based on the previous three-dimensional volume data is corrected by the amount of displacement.

Consequently, even when the image based on the previous three-dimensional volume data is referred to, the scanning region reflecting the present on-bed placement state of the subject P is set.

The previous image for measuring the amount of displacement may be an image based on previous three-dimensional volume data, or may be a previous scout image captured in pre-scan for capturing the previous three-dimensional volume data. In the present embodiment, the description is made by using a scout image with which measurement of the amount of displacement is easy. In a case where an image based on three-dimensional volume data is used as a previous image for measuring the amount of displacement, data of the same plane as the scout image is extracted from the three-dimensional volume data, and an image represented by the data is used. Moreover, by using two types of scout images captured from two orthogonal directions, it is possible to measure the amount of displacement in each direction of three dimensions and obtain the accurate amount of displacement. Therefore, the present embodiment is described on the premise of dual scanograms. However, it is also possible to measure the amount of displacement by using a scout image of only a single direction, and it is possible to create a scanning plan with reference to an image based on previous three-dimensional volume data.

Figure 2:
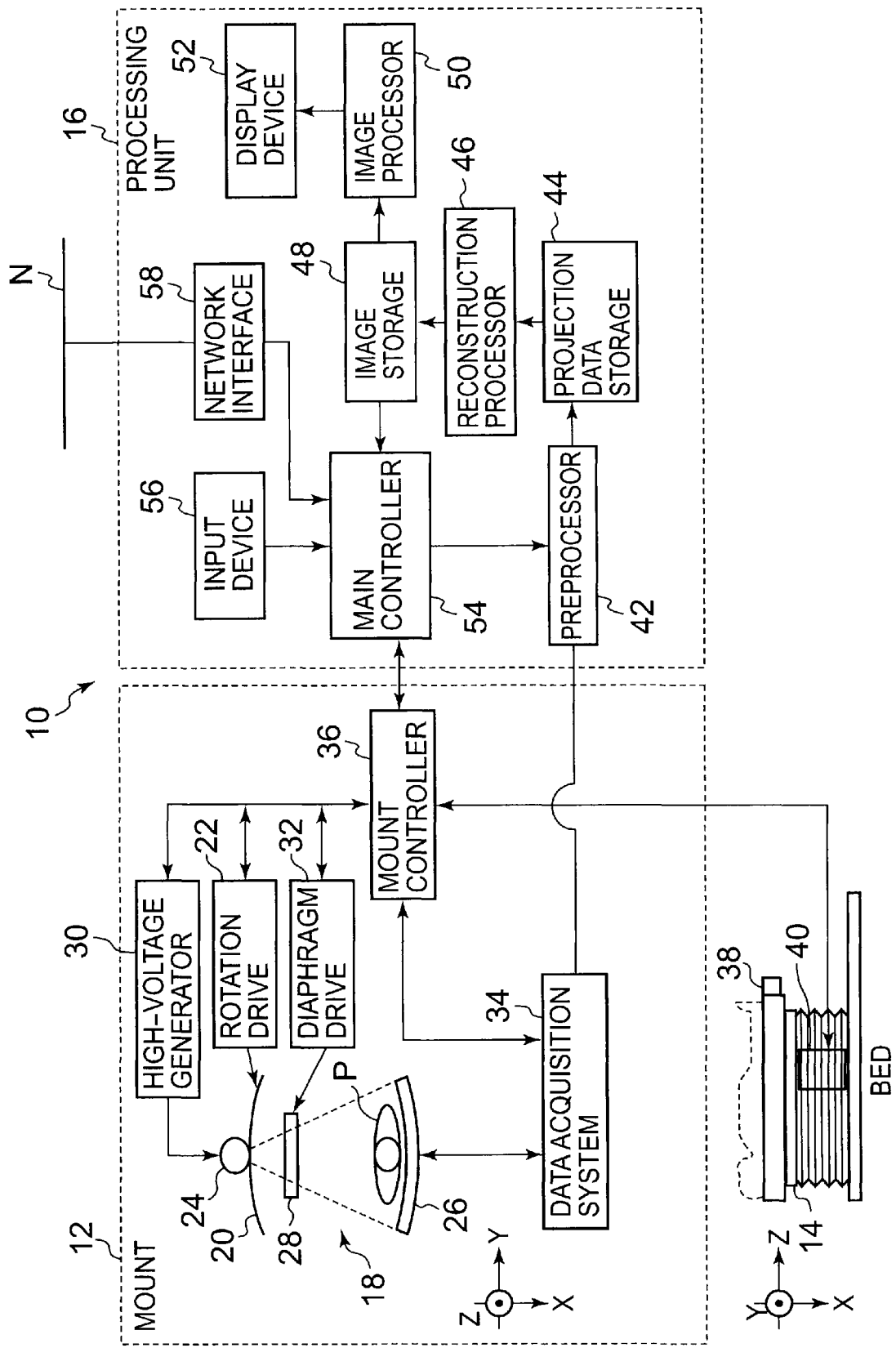
FIG. 2 shows the configuration of the X-ray CT system.

FIG. 2 is a diagram showing the configuration of the X-ray CT system 10. This X-ray CT system 10 continuously changes the X-ray irradiation position around the body axis of the subject P or in the direction of the body axis to collect projection data reflecting the transmission amount of the X-ray from the subject P and reconstruct the projection data, thereby acquiring data that represents the inside of the body of the subject P.

The X-ray CT system 10 includes a mount 12, a bed 14, and a processing unit 16. The mount 12 is a capturing part that irradiates the subject P with X-rays from a plurality of directions and detects the X-ray transmitted through the subject P. Moreover, the mount 12 also serves as a capturing part that captures a scout image of the subject P by irradiating the subject P with an X-ray from a single direction to the body axis direction and detecting the X-ray transmitted through the subject P.

This mount 12 has an aperture 18 into which the subject P is inserted. The bed 14 is a device that inserts the subject P into the aperture 18. The processing unit 16 is a device that generates scanning plan data for controlling the drive of the mount 12 and the bed 14 to integrally control the mount 12 and the bed 14, and executes an image reconstruction process on X-ray transmission data, thereby generating and displaying an image of the inside of the subject P. The scanning plan data is sequence data representing a scanning plan that defines at least one of the scanning region and the tube current or both of them.

The mount 12 houses a gantry 20 and a rotation drive 22 therein.

The gantry 20 is a ring body that can rotate about the aperture 18. The rotation drive 22 is composed of a motor and a gear or the like that has an interlocking relationship with the gantry 20, and rotates the gantry 20 about the aperture 18.

On the gantry 20, an X-ray tube 24 and an X-ray detector 26 are installed facing each other across the aperture 18. Moreover, on the gantry 20, a collimator 28 is disposed between the X-ray tube 24 and the X-ray detector 26. Inside the mount 12, a high-voltage generator 30 is disposed in pair with the X-ray tube 24, a diaphragm drive 32 is disposed in pair with the collimator 28, and a data acquisition system 34, which is called DAS (data acquisition system), is disposed in pair with the X-ray detector 26.

Further, the mount 12 is provided with a mount controller 36, which is a scanning controller on the side of the mount 12. This mount controller 36 controls the high-voltage generator 30, the diaphragm drive 32, the data acquisition system 34 and the bed 14 in accordance with the scanning plan data. That is, the mount controller 36 sends a control signal for controlling a tube current to the high-voltage generator 30, in accordance with information representing the tube current contained in the scanning plan data. The mount controller sends a control signal for controlling an irradiation field to the diaphragm drive 32, in accordance with information representing the range of the irradiation field contained in the scanning plan data. The mount controller sends control signals for controlling a movement starting position, a movement velocity and a movement ending position to the bed 14, in accordance with information representing the scanning region contained in the scanning plan data.

The high-voltage generator 30 supplies an electric current for heating a filament to the X-ray tube 24 and applies a high voltage. As the high-voltage generator 30, a high-frequency inverter type is applied, which is a type of rectifying alternating current power of 50/60 Hz into a direct current, converting it to a high-frequency alternating current of several kHz or more to boost the pressure, and rectifying it again to apply it. The X-ray tube 24 receives the supply of the electric current and the application of the high voltage and generates an X-ray. The collimator 28 is driven by the diaphragm drive 32 to define the irradiation field of the X-ray and block X-rays outside the irradiation field, thereby narrowing the X-ray generated by the X-ray tube 24 down to a fan-shaped or cone-shaped beam. The X-ray detector 26 is provided with multivariate and multichannel X-ray detecting elements arrayed in two orthogonal directions. The array shape is an arc shape around the focal point of the X-ray generated by the X-ray tube 24. The mainstream X-ray detecting element is an indirect conversion type that converts an X-ray into light by a phosphor such as a scintillator and further converts the light into a charge by a photoelectric conversion element such as a photodiode, and a direct conversion type using generation of an electron-hole pair in a semiconductor by an X-ray and movement thereof to an electrode, namely, using a photoconductive phenomenon. This X-ray detector 26 detects the X-ray transmitted through the subject P, and outputs an X-ray transmission signal reflecting the transmission amount of the detected X-ray, for each of the X-ray detecting elements. The data acquisition system 34 collects the X-ray transmission signals from the respective X-ray detecting elements every time the control signal is inputted from the mount controller 36. For each of the radiation detecting elements, an I-V converter, an integrator, a preamplifier and an A/D converter are provided to convert a current signal from each of the radiation detecting elements into a voltage signal, integrate the voltage signal in synchronization with the radiation exposure period, amplify, and convert into a digital signal. The data acquisition system 34 outputs the X-ray transmission signals converted into digital signals to the processing unit 16. The X-ray transmission signals outputted from the data acquisition system 34 are digital data containing the value of the integer of each absorption coefficient along the transmission length of the X-ray sequentially transmitted through materials with different X-ray absorption coefficients. It is so-called raw data.

The bed 14 is provided with a top board 38 for placing the subject P and a bed driving part 40. The top board 38 is driven by the bed driving part 40 to slide in a long-side direction (a Z-axis direction in the drawing) to be inserted into the aperture 18. In the processing unit 16, a preprocessor 42, a projection data storage 44, a reconstruction processor 46, an image storage 48, an image processor 50, and a display device 52 are sequentially connected and implemented. Moreover, a main controller 54, an input device 56, and a network interface 58 are disposed in the processing unit 16.

The preprocessor 42 executes sensitivity correction on raw data.

The raw data having been subjected to the sensitivity correction is called projection data, which is inputted and stored in the projection data storage 44. The reconstruction processor 46 mainly uses a reconstruction algorithm called the Feldkamp method to read out the corrected projection data from the projection data storage 44, followed by back projection, and reconstructs the inside of the subject P as image data. The reconstructed image data is inputted and stored in the image storage 48. The image processor 50 subjects image data stored in the image storage 48 to a variety of image processing such as scan conversion of converting into a video format of the orthogonal coordinate system to generate a display image. The display device 52 is a monitor such as a liquid crystal display or a CRT display, which displays a display image that has been generated by the image processor 50. The main controller 54 is a scanning controller on the console side that generates scanning plan data according to operation via the input device 56 and outputs it to the mount controller 36. The input device 56 is a pointing device such as a trackball or a mouse having a click button that moves a cursor displayed on the display device 52 for selecting a button or menu option via a GUI, or a keyboard that inputs symbol strings such as numbers and characters.

The network interface 58 constitutes equipment such as a LAN card, a LAN board, or a LAN adaptor comprising a connector for connecting the cable of a network adaptor, and a circuit required for connecting to the network in compliance to LAN standards such as Ethernet.

Figure 3:
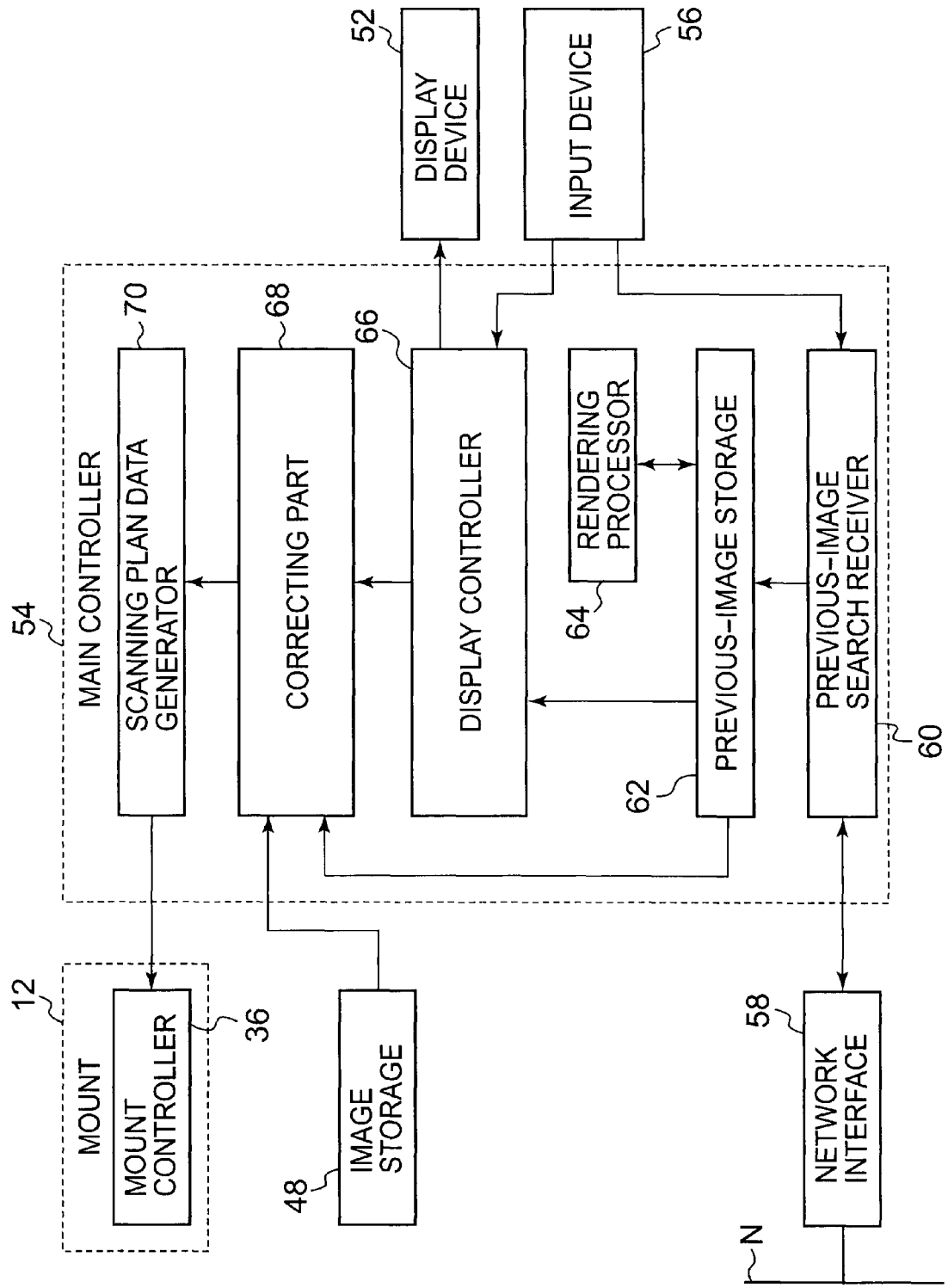
FIG. 3 shows a more detailed configuration relating to creation of a scanning plan of a main controller.

FIG. 3 is a block diagram showing a more detailed configuration relating to creation of a scanning plan of the main controller 54. The main controller 54 has a previous-image search receiver 60, a previous-image storage 62, a display controller 66, a rendering processor 64, a correcting part 68, and a scanning plan data generator 70. The respective parts may be composed of dedicated circuits, or may be functionally achieved through execution of a program by a CPU.

The previous-image search receiver 60 causes the image archive apparatus 1 to search a previous image of the subject P, and receives the previous image of the subject P from the image archive apparatus 1.

The previous-image search receiver 60 sends a search key that specifies the subject P inputted by using the input device 56 to the image archive apparatus 1, thereby causing the image archive apparatus 1 to search. The transmission of the search key and the reception of the previous image are conducted via the network interface 58 and the network N. The received previous image is stored in the previous-image storage 62.

Among the previous images of the subject P, the display controller 66 reads out a three-dimensional image based on three-dimensional volume data and a cross-sectional image (an MPR image cut into round slices along the XY plane in the drawing) from the previous-image storage 62, and controls the display device 52 to display them. Moreover, in response to an operation of inputting the scanning region with the input device 56, the display controller 66 controls to display position mark information that represents the scanning region within the three-dimensional image and on the cross-sectional image. The position mark information displayed within the three-dimensional image is represented with a circular cylindrical frame body, and the position mark information displayed on the cross-sectional image is represented with a circular frame body. When the operator moves the scanning region or performs an operation of enlarging or shrinking it by using the input device 56, the display controller 66 controls to move, or enlarge or shrink the position mark information within the three-dimensional image and on the cross-sectional images, in response to the input operation.

The rendering processor 64 executes a volume rendering process on the three-dimensional volume data stored in the previous-image storage 62 to generate a three-dimensional image and a cross-sectional image. In a case where the previous-image storage 62 stores no three-dimensional image or cross-sectional image, i.e., in a case where the image archive apparatus 1 stores no three-dimensional image and stores only three-dimensional volume data and the previous-image search receiver 60 receives a scout image and three-dimensional volume data alone as a previous image, volume rendering is performed.

The correcting part 68 corrects the position of the scanning region inputted with the input device 56 so as to match the on-bed placement state of the subject P for scan this time. First, from a scout image captured beforehand for generating scanning plan data of actual scan this time and a scout image stored in the previous-image storage 62, the correcting part 68 calculates the amount of displacement of the subject shown in the scout images. Then, the correcting part shifts the position of the scanning region inputted with the input device 56 by this displacement amount.

The scanning plan data generator 70 generates scanning plan data containing information showing the corrected scanning region, and sends it to the mount controller 36.

Figure 4:
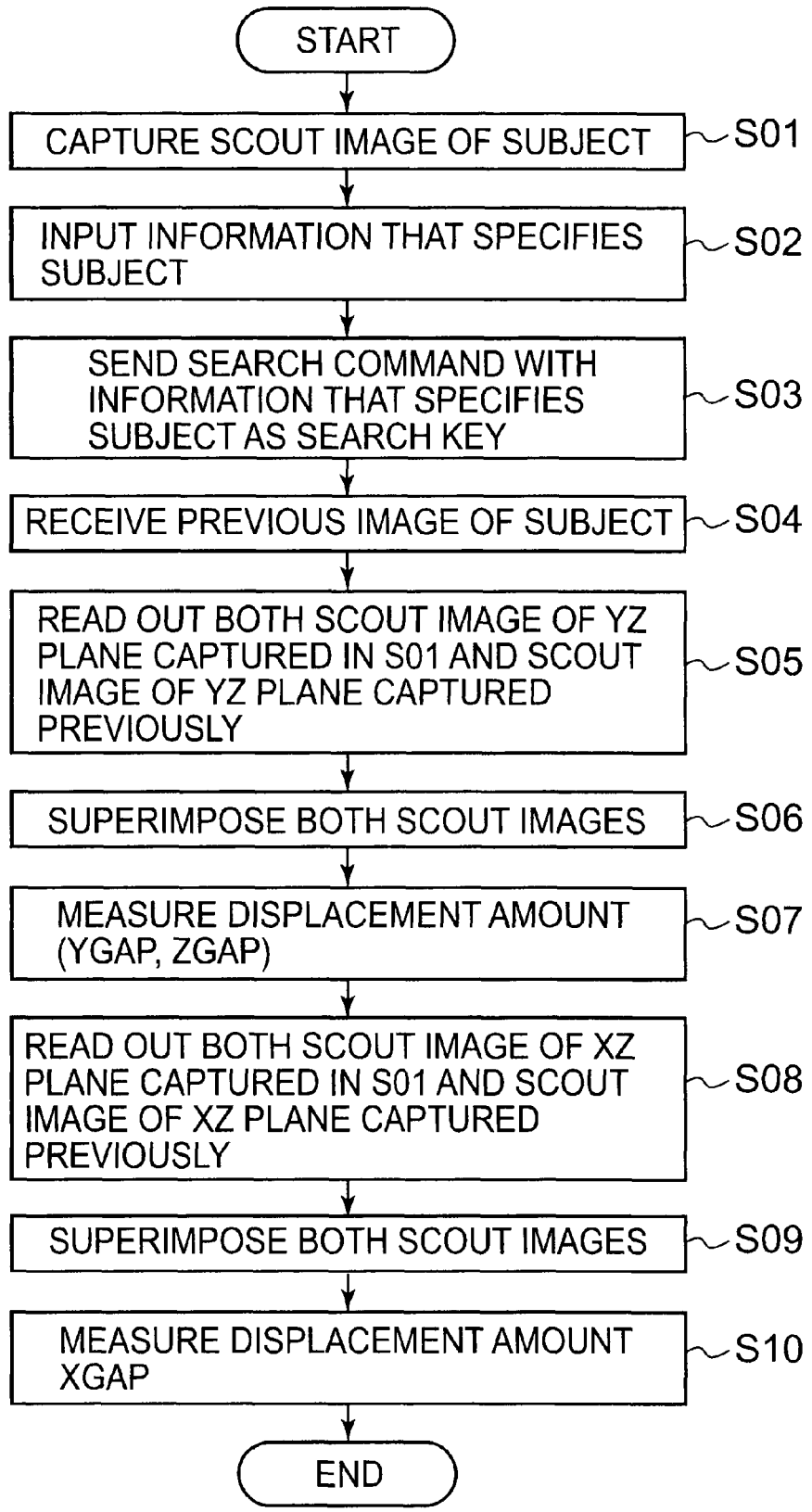
FIG. 4 is a flowchart showing a process of measuring the amount of displacement by the main controller.

FIG. 4 is a flowchart showing a process of measuring the amount of displacement by the main controller 54.

First, the subject P is placed on the top board 38, and a scout image of the placed subject P is captured (S01). In capturing the scout image, the main controller 54 first generates scanning plan data for creation of scout images from two orthogonal directions, such as the front, i.e., the YZ plane, and the side, i.e., XZ plane. The main controller 54 outputs this created scanning plane data to the mount controller 36. The mount controller 36 starts control to capture a scout image of the subject P placed on the top board 38 in accordance with the inputted scanning plan data. The mount controller 36 into which the scanning plan data for scout image creation has been inputted outputs a control signal to the rotation drive 22, and rotates and fixes the X-ray tube 24 so as to face the front of the subject P, i.e., the YZ plane. Then, while a control signal for rotation is not outputted to the rotation drive 22 that rotates the gantry 20, drive signals are outputted to the high-voltage generator 30, the diaphragm drive 32, the data acquisition system 34, and the bed-driving part 40. As the X-ray tube 24 and the X-ray detector 26 are fixed in front of the subject P, the top board 38 is moved in the Z-axis direction and irradiated with an X-ray, whereby the front of the subject P is irradiated with the X-ray along the body axis direction, and a scout image of the YZ plane is captured from the front of the subject P. Next, the mount controller 36 returns the top board 38 to the origin position, outputs a control signal to the rotation drive 22, and rotates the X-ray tube 24 by 90 degrees to fix so as to face the side of the subject P, i.e., the XZ plane. Then, the top board 38 is moved in the Z-axis direction and irradiated with an X-ray, whereby the side of the subject P is irradiated with the X-ray along the body axis direction, and a scout image of the XZ plane is captured from the side of the subject P. The scout images of the YZ plane and the XZ plane of the subject P are collected by the data acquisition system 34 and stored in the image storage 48.

When information that specifies the subject P is inputted with the input device 56 around the time when the scout images are captured (S02), the previous-image search receiver 60 sends a search command with the information specifying the subject P as a search key to the image archive apparatus 1 via the network interface 58 and the network N (S03). Then, a previous image of the subject P is received from the image archive apparatus 1 (S04). The information specifying the subject P is, for example, a patient ID or a patient's name. The previous-image search receiver 60 causes the previous-image storage 62 to store the received previous image.

FIG. 5 is a data configuration view showing a database for searching a previous image. As shown in FIG. 5, the image archive apparatus 1 stores subject information that specifies the subject P, capturing date information that represents the date when a previous image is captured, site information that represents a site where a previous image is captured, and archive destination information that represents the destination to archive a previous image, so as to be linked with each other. When receiving information that specifies the subject P, the image archive apparatus 1 searches a record containing the information specifying the subject P from the database, and sends a list of the records containing the information specifying the subject P to the X-ray CT system 10. When receiving the list of the records, the previous-image search receiver 60 causes the display device 52 to display this list. When one of the records is selected from the list with the input device 56, the previous-image search receiver 60 sends a request for sending the previous image that is the main constituent of this record. When receiving this sending request, the image archive apparatus 1 reads out the archive destination information of the previous image from the requested record, and sends the previous image stored in the storage destination to the X-ray CT system 10.

After the scout image is captured and the previous image is received, the correcting part 68 reads out a scout image of the YZ plane captured at S01 and a scout image of the YZ plane contained in the previous image from the image storage 48 and the previous-image storage 62 (S05), superimposes the two scout images with each other (S06), and measures the amount of displacement in the Y-axis direction and Z-axis direction (Ygap, Zgap) of the images of the subject P shown in both the scout images (S07).

Figure 6:
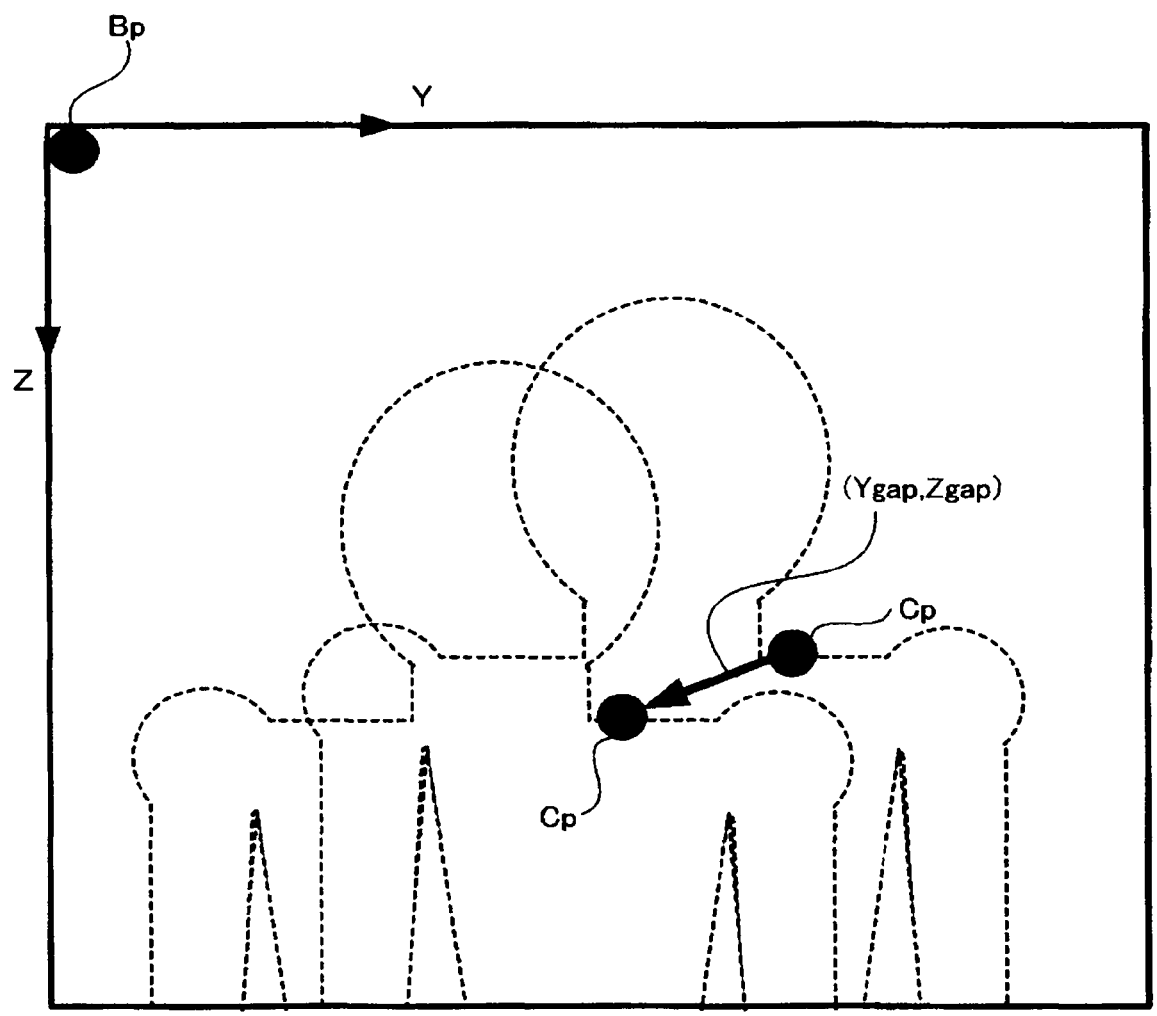
FIG. 6 shows a state in which a scout image of a YZ plane captured previously and a scout image of the YZ plane captured this time are superimposed.

FIG. 6 is a view showing a state in which a previous scout image of the YZ plane and a scout image of the YZ plane captured this time are superimposed. The two scout images are superimposed so that reference points Bp coincide. As the reference points Bp, the correcting part 68 makes the origins of the two images coincide. In general, an image is captured so that a specific point on the top board 38 corresponds to the origin position of the image. Because an on-bed placement state at the time of capture of a previous scout image is different from an on-bed placement state at the time of capture of a scout image this time, displacement occurs in the images of the subject P when they are superimposed so that the reference points Bp coincide.

The correcting part 68 extracts a portion having a characteristic shape easy to extract, such as the left collarbone portion, as a common site Cp from each of the scout images. Then, a coordinate difference Ygap in the Y-axis direction and a coordinate difference Zgap in the Z-axis direction of both pixels composing the left collarbone portion are measured. The measured value is stored as the amount of displacement in the Y-axis and Z-axis directions (Ygap, Zgap).

Furthermore, the correcting part 68 reads out the captured scout image of the XZ plane and the scout image of the XZ plane contained in the previous image (S08), superimposes the two scout images (S09), and measures the amount of displacement Xgap in the X-axis direction of the subject P shown in both the scout images (S10).

Figure 7:
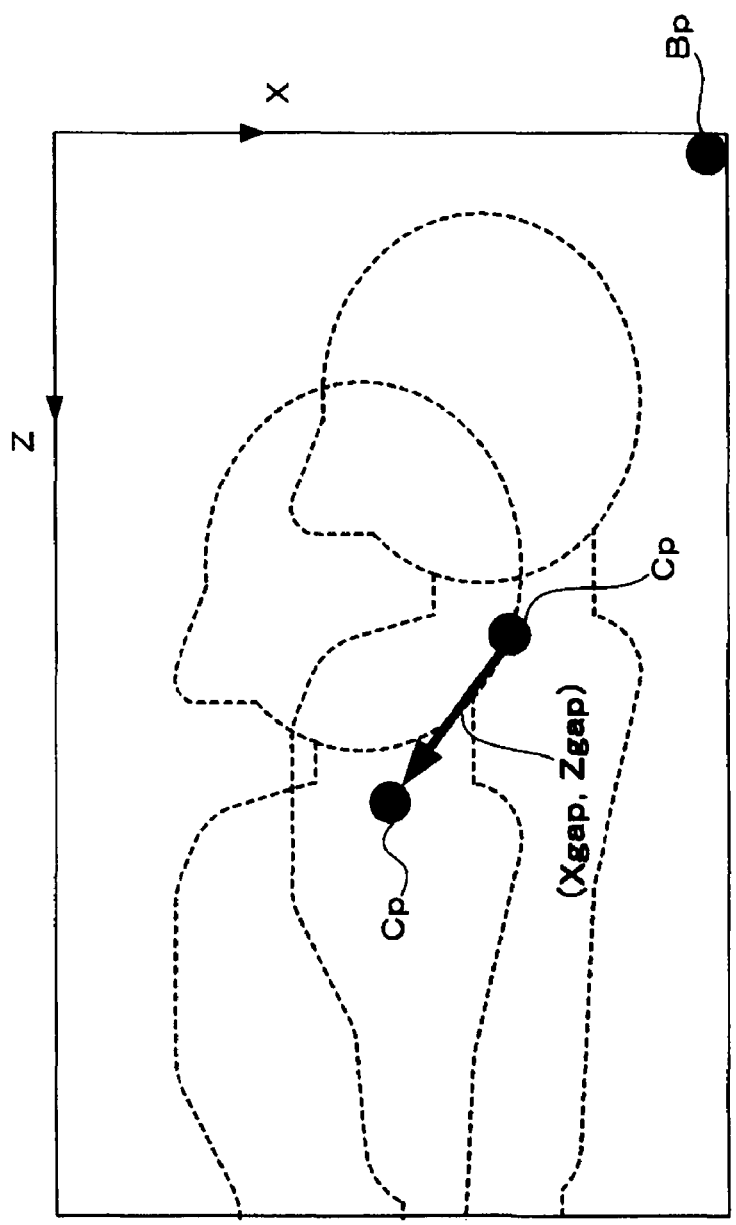
FIG. 7 shows a state in which a scout image of an XZ plane captured previously and a scout image of the XZ plane captured this time are superimposed.

FIG. 7 is a view showing a state in which a previous scout image of the XZ plane and a scout image of the XZ plane captured this time are superimposed. The two scout images are superimposed so that the reference points Bp coincide. As the reference points Bp, the correcting part 68 makes the origins of both the images coincide. The correcting part 68 extracts a portion having a characteristic shape easy to extract, such as the left collarbone portion, as the common site Cp from each of the scout images, and measures a coordinate difference Xgap on the X-axis in both pixels composing the left collarbone portion. This measured value is stored as the amount of displacement Xgap in the X-axis direction.

Figure 8:
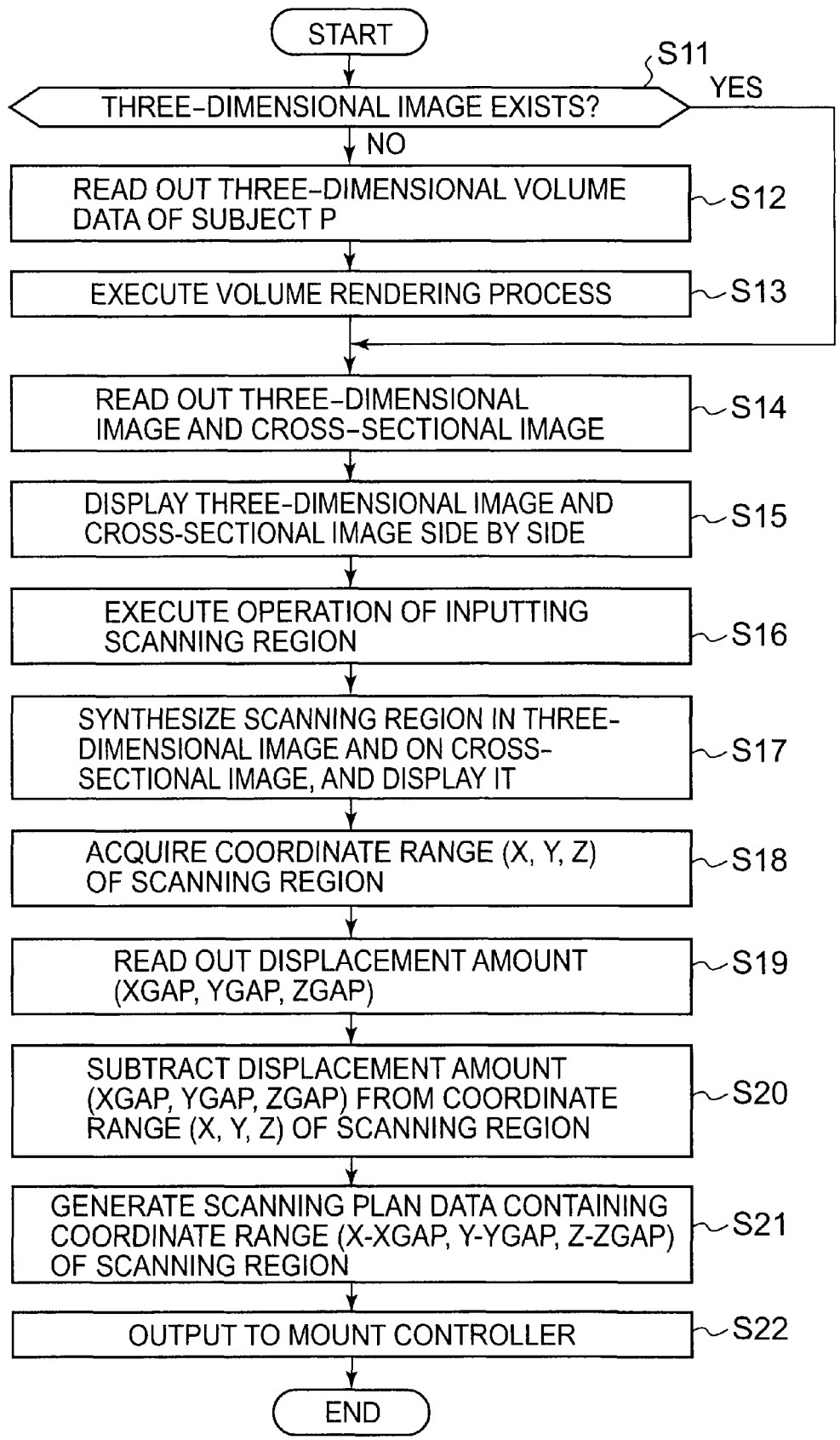
FIG. 8 is a flowchart showing a process of correcting a scanning region by the amount of displacement.

Next, a process of correcting the scanning region inputted into the previous three-dimensional image on the basis of the obtained amount of displacement (Xgap, Ygap, Zgap) so as to reflect the current on-bed placement state of the subject P will be described with reference to FIG. 8. FIG. 8 is a flowchart showing the process of correcting the scanning region by the amount of displacement. First, the rendering part 64 searches whether any three-dimensional image of the subject P exists in the previous-image storage 62 (S11). In a case where no three-dimensional image exists in the previous-image storage 62 (S11, No), the rendering part 64 reads out three-dimensional volume data of the subject P from the previous-image storage 62 (S12), and generates a three-dimensional image by performing volume rendering (S13). In a case where the previous-image storage 62 stores no cross-sectional image of the subject P as well, the rendering part 64 also generates a cross-sectional image by executing an MPR process on the three-dimensional volume data.

In a case where a three-dimensional image exists in the previous-image storage 62 (S11, Yes), or when a three-dimensional image is generated by the rendering part 64 (S13), the display controller 66 reads out a three-dimensional image and a cross-sectional image from the previous-image storage 62 (S14), and generates a display image in which the three-dimensional image and the cross-sectional image are put side by side to control the display device 52 to display them (S15). When an operation of inputting the scanning region is executed with the input device 56 (S16), the display controller 66 generates a display image in which position mark information representing the scanning region is synthesized on the three-dimensional image and the cross-sectional image to cause the display device 52 to display them (S17).

Figure 9:
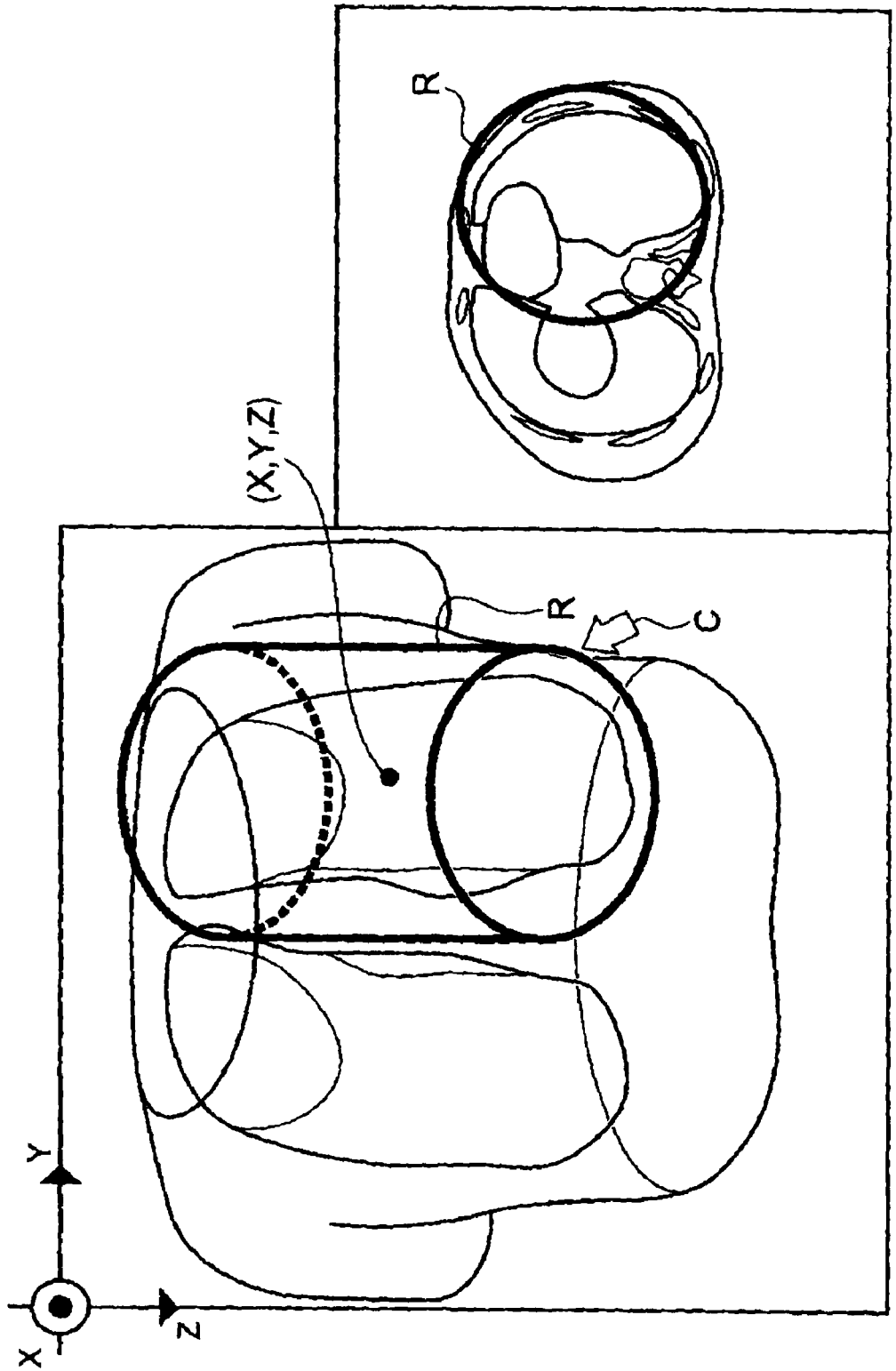
FIG. 9 is a schematic view showing an image based on displayed three-dimensional volume data.

FIG. 9 is a schematic view showing a displayed three-dimensional image. A previous cross-sectional image is displayed side by side with a previous three-dimensional image. On the three-dimensional image, a cylindrical frame body representing a scanning region R is displayed as position mark information. This scanning region R is displayed by moving a cursor C on the screen to one corner of a site desired to input as the scanning region R by a mouse or a trackball of the input device 56 and moving the cursor C while dragging it to the other corner. The display controller 66 generates a display image in which the starting and ending points are included in the outer shell and a cylindrical frame body having the center of gravity at the midpoint between the starting point and the ending point is synthesized in the image based on the three-dimensional volume, and controls the display device 52 to display the display image. For example, when desiring to set a region containing the left lung field of the subject P as the scanning region R, the operator operates the input device 56 so as to encompass the left lung field. The display controller 66 synthesizes the cylindrical frame body encompassing the left lung field into the image based on the three-dimensional volume, and controls the display device 52 to display it.

Further, the display controller 66 synthesizes a circular or square frame body representing the range of the scanning region R contained in a cross-sectional image including one end face of the scanning region R, generates a display image in which the frame body is put with the three-dimensional image, and controls the display device 52 to display the display image. Moreover, a button (not shown) for turning cross-sectional images is displayed on the screen. When this button is pressed down, the display controller 66 reads out a next cross-sectional image closer to the other end face of the scanning region R than the currently displayed cross-sectional image from the previous-image storage 62, superimposes the frame body representing the range of the scanning region R contained in that cross-sectional image, and generates a display image in which the frame body is put with the three-dimensional image, thereby controlling the display device 52 to display the display image.

When the scanning region is displayed in the image based on the three-dimensional volume by the display controller 66, the correcting part 68 acquires the coordinate range (X, Y, Z) of the scanning region in the image based on the three-dimensional volume (S18). For example, when the scanning region is set so as to encompass the left lung field of the subject P, the correcting part 68 acquires the coordinate range on the three-dimensional volume data coordinate system of the frame body encompassing the left lung field.

When the coordinate range (X, Y, Z) of the scanning region in the three-dimensional volume data is acquired, the correcting part 68 reads out the amount of displacement (Xgap, Ygap, Zgap) (S19), and subtracts the amount of displacement (Xgap, Ygap, Zgap) from the acquired coordinate range (X, Y, Z) of the scanning region, thereby correcting the scanning region on the coordinate system of the scout image captured this time. Consequently, the coordinate range (X-Xgap, Y-Ygap, Z-Zgap) of the scanning region reflecting the current on-bed placement state is acquired (S20). The scanning plan data generator 70 generates scanning plan data containing the coordinate range (X-Xgap, Y-Ygap, Z-Zgap) of the corrected scanning region (S21), and outputs it to the mount controller 36 (S22).

Figure 10:
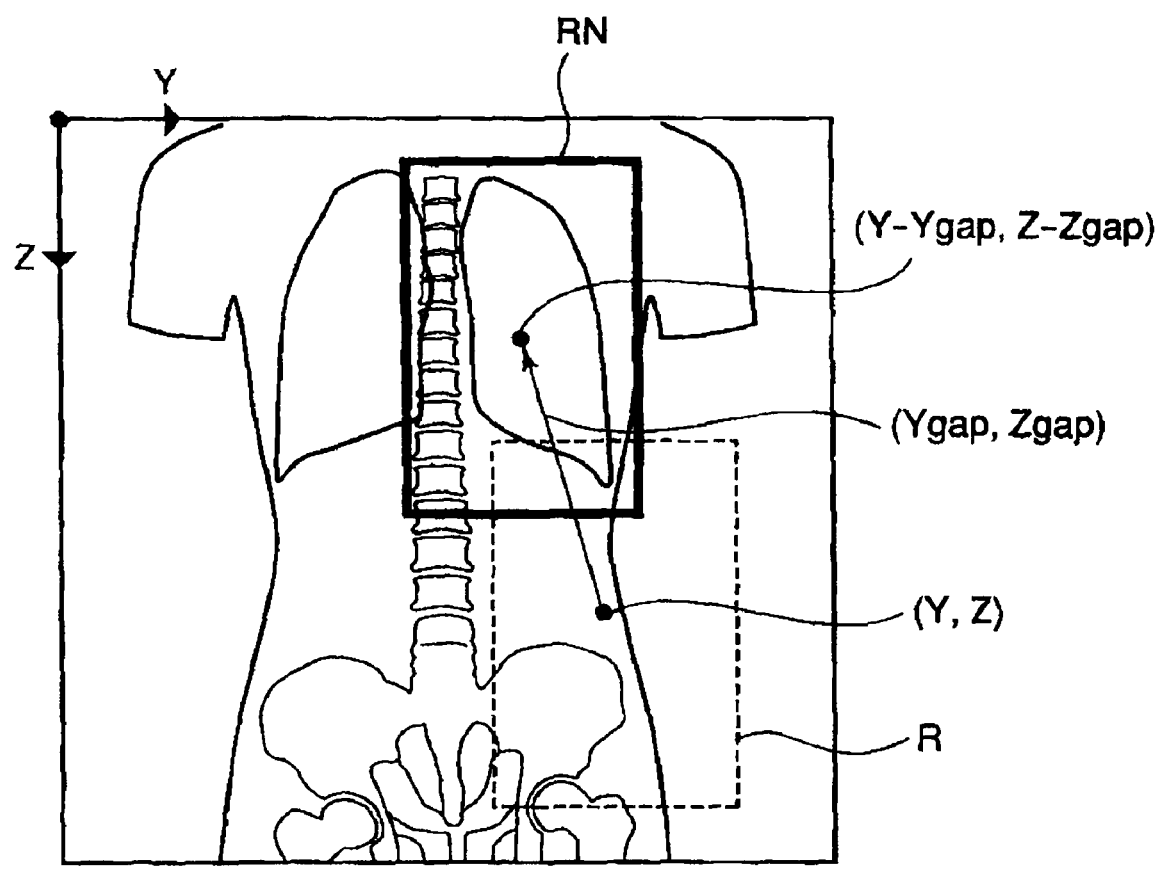
FIG. 10 shows a scout image of the YZ plane captured this time.
Figure 11:
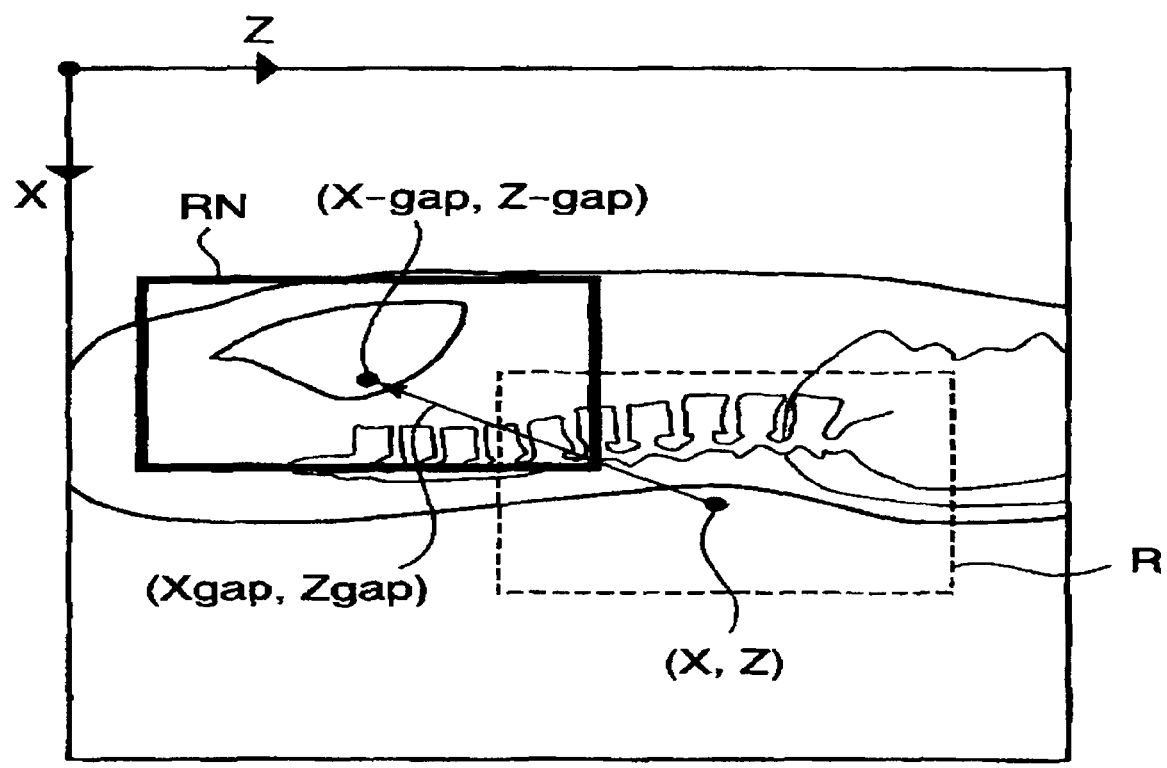
FIG. 11 shows a scout image of the XZ plane captured this time.

FIG. 10 and FIG. 11 are schematic views showing scout images captured this time. FIG. 10 shows a scout image of the YZ plane, and FIG. 11 shows a scout image of the XZ plane. The scout images captured this time represent the current on-bed placement state of the subject P. For example, the scanning region R is matched with the left lung field of the subject P shown in the image based on the previous three-dimensional volume, and the coordinate range (X, Y, Z) in the three-dimensional volume data of this scanning region R is applied to the scout image captured this time without modification. Then, the left lung field of the subject P in the current on-bed placement state of is not included in the applied scanning region.

However, when the correcting part 68 shifts the coordinate range (X, Y, Z) in the three-dimensional volume data by the measured amount of displacement (Xgap, Ygap, Zgap), the left lung field of the subject P in the current on-bed placement state is included in the range indicated by the coordinate range of a corrected scanning region RN (X-Xgap, Y-Ygap, Z-Zgap) on the scout image that has been captured this time. By calculating the bed position from the coordinate range showing the corrected scanning region RN (X-Xgap, Y-Ygap, Z-Zgap), even if the scanning region R is set using the image based on the past three-dimensional image, the bed 14 may be driven according to the current state of being placed on the bed for defining the irradiation field.

Thus, in the X-ray CT system 10 according to the present embodiment, the amount of displacement (Xgap, Ygap, Zgap) of the subject P between the previous image and the current scout image is measured beforehand and, when the scanning region is inputted in an image based on the previous three-dimensional volume, the coordinate range (X, Y, Z) of this scanning region is corrected by the amount of displacement (Xgap, Ygap, Zgap). Then, actual scanning of irradiating the scanning region after the position correction (X-Xgap, Y-Ygap, Z-Zgap) with an X-ray is performed. Consequently, the scanning region can be inputted by using the image based on the previous three-dimensional volume of the subject P, whereby it is possible to present a capturing site such as an organ to the operator more accurately than with a scanning plan based on an X-ray transmission image.

Accordingly, it is no longer necessary for the operator to estimate the spatial position, and the scanning region can be determined with precise accuracy.

The above description is based on dual scanograms, but as previously described, it is possible to capture only a scout image of the front of the subject P, i.e., the YZ plane, and calculate the amount of displacement (Xgap, Ygap, Zgap). The amount of displacement in the X direction, i.e., in the direction of the bed height, depends on the height of the bed 14, because the height of the subject P from the height above the top board of the bed 14 will not change. Information that represents the height of the bed 14 is incidental to an image in the DICOM standard. Therefore, the correcting part 68 calculates the amount of displacement Xgap on the basis of the inputted height of the bed 14 and the height of the bed 14 that is incidental to a previous image.

Further, an aspect of inputting the range of the scanning region to an image based on the previous three-dimensional volume data is described above. However, it is also possible to configure so that the shape of an organ shown in an image based on three-dimensional volume data is recognized and a scanning region matched to the organ is automatically inputted within the image based on the three-dimensional volume data.

Figure 12:
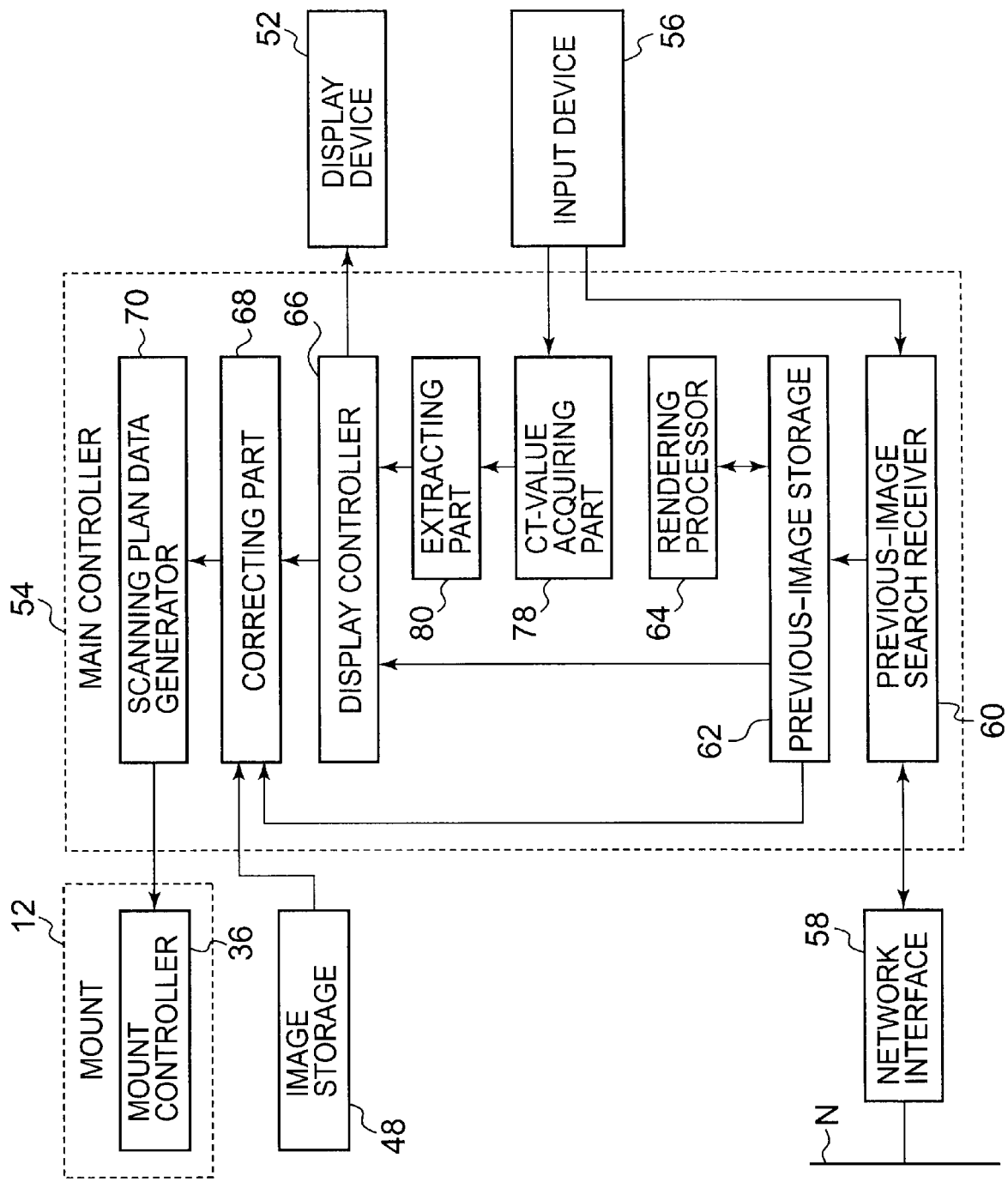
FIG. 12 shows a detailed configuration of a main controller that automatically inputs a scanning region into an image based on three-dimensional volume data.

FIG. 12 is a block diagram showing a detailed configuration of the main controller 54 that automatically inputs the scanning region into the image based on the three-dimensional volume data. The same configuration will be provided with the same name and the same reference numeral, and a detailed explanation thereof will be omitted.

In the X-ray CT system 10 that automatically inputs the scanning region into the image based on the three-dimensional volume data, the main controller 54 further has a CT-value acquiring part 78 and an extracting part 80, in addition to the display controller 66.

When a single point within an image based on three-dimensional volume data is designated, the CT-value acquiring part 78 acquires the CT value of the designated position. The CT value represents an X-ray absorption coefficient as a relative value with reference to water in general. This CT value is expressed by $[(\mu-\mu_0)/\mu_0] \times K$, wherein $\mu$ is an absorption coefficient of a material, $\mu_0$ is an absorption coefficient of a reference material and K is a constant. In general, the CT value of water is 0, and K is equal to 1,000, so the CT value of air is −1,000. In three-dimensional volume data, a pixel value of a pixel corresponds to the CT value. That is, the CT-value acquiring part 78 acquires the CT value of the designated position. The single point within the image based on the three-dimensional volume data is designated through an operation with the input device 56. When a trackball or a mouse of the input device 56 is operated to move a cursor within a display screen of the display device 52 to a designated position and is clicked, the CT value of the pixel corresponding to the clicked coordinate position is read out.

The extracting part 80 extracts the outline of a tissue such as an organ containing the designated single point within the image based on the three-dimensional volume data. The collection of pixels having substantially the same CT value as the CT value of the designated single point within the image based on three-dimensional volume data is extracted by the region expansion method, and the coordinate of each of the pixels composing the outline of the region. The range of substantially the same CT value is a predetermined range centered on the CT value of the designated single point. This range is stored beforehand in an internal ROM of the extracting part 80.

The display controller 66 generates a scanning region that includes the region extracted by the extracting part 80, and synthesizes it into the image based on the three-dimensional volume data to control the display device 52 to display. In the main controller 54, the correcting part 68 corrects the position of the scanning region that includes the extracted region extracted by the extracting part 80, and the scanning plan data generator 70 makes the scanning region after the position correction contained in the scanning plan data to be sent to the mount controller 36.

Figure 13:
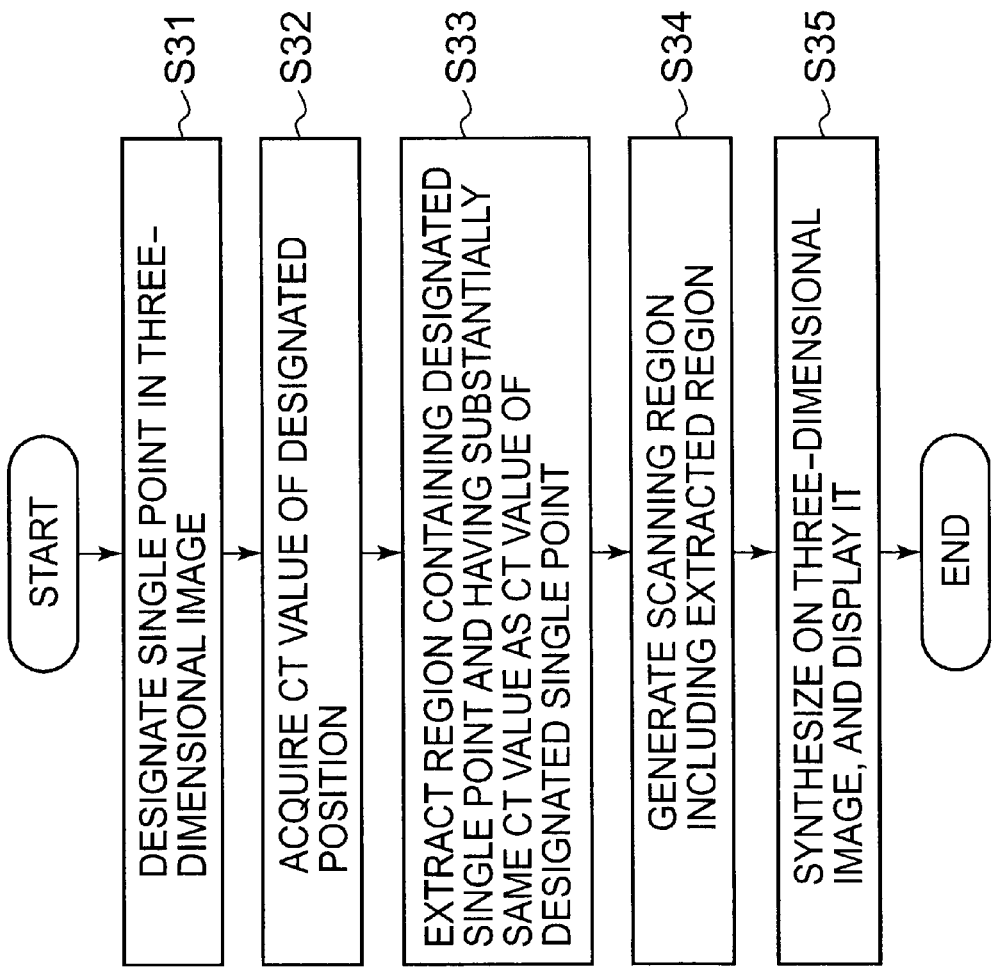
FIG. 13 is a flowchart showing a process of automatically inputting a scanning region into an image based on three-dimensional volume data.
Figure 14:
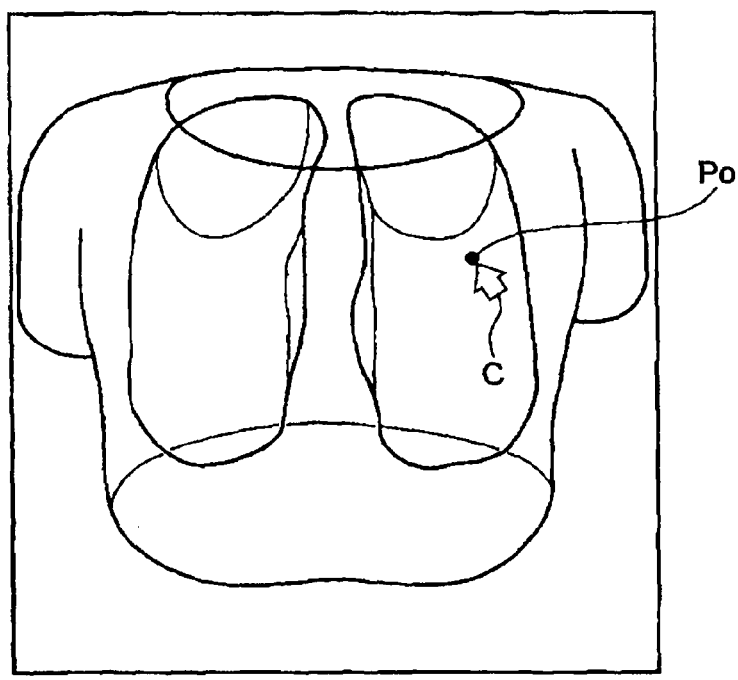
FIG. 14 shows an aspect of designating a single point in the image based on the three-dimensional volume data.

FIG. 13 is a flowchart showing a process of automatically inputting the scanning region into the image based on the three-dimensional volume. First, as shown in FIG. 14, when a single point Po within the image based on the three-dimensional volume data is designated with the input device 56 (S31), the CT-value acquiring part 78 acquires the CT value of the designated point Po within the image based on the three-dimensional volume data (S32).

Figure 15:
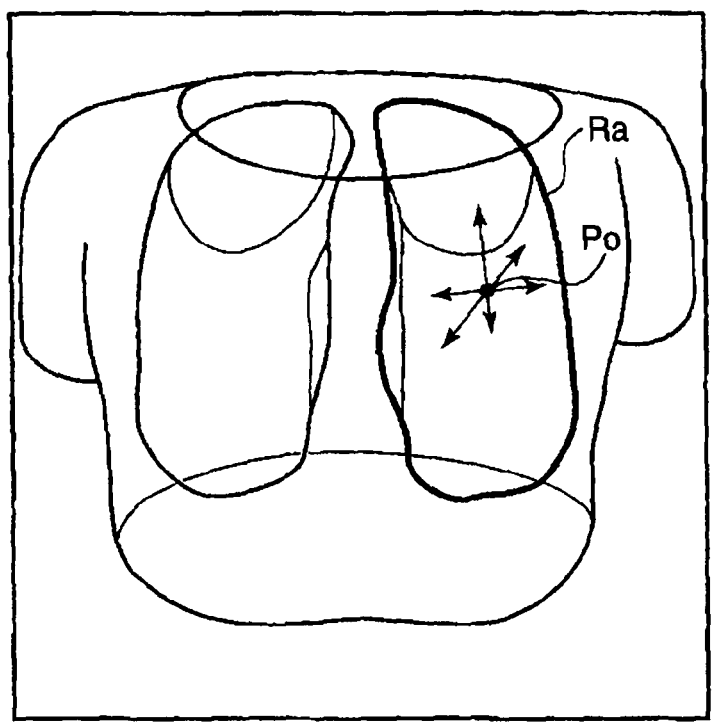
FIG. 15 shows an aspect of extracting a region by region expansion from the designated single point in the image based on the three-dimensional volume data.

When the CT value of the designated single point Po is acquired, the extracting part 80 extracts a region that contains the designated single point Po and has substantially the same CT value as the CT value of the designated single point Po (S33). As shown in FIG. 15, while expanding a search region around the designated single point, the extracting part 80 compares the CT value of a search target pixel with the acquired CT value. Then, in a case where the CT value of the search target pixel is included in the predetermined range where the CT value is substantially the same as the acquired CT value, this search target pixel is included in an extracted region Ra. Extraction ends if all of the search target pixels have the CT values outside the predetermined range after expansion of the search region.

Figure 16:
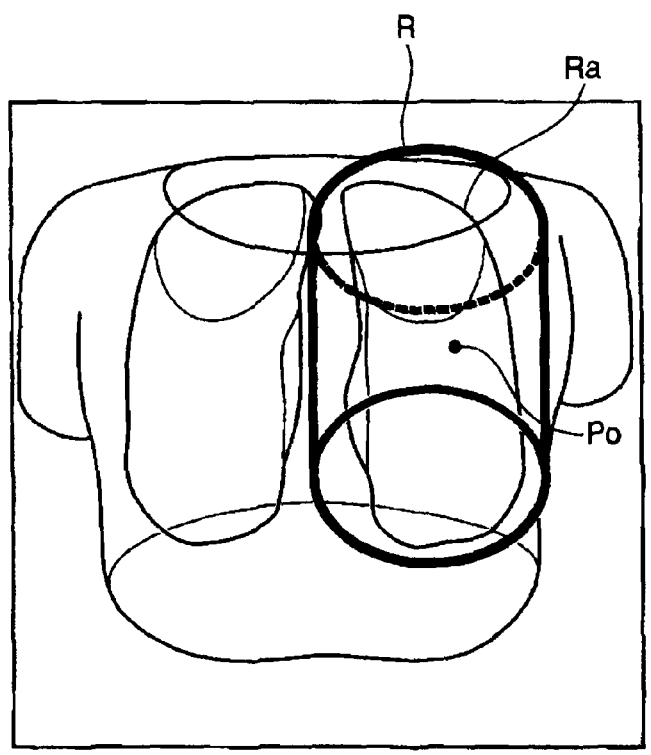
FIG. 16 shows an aspect of generating a scanning region including the extracted region in the image based on the three-dimensional volume data.

When the region is extracted, as shown in FIG. 16, the display controller 66 generates the scanning region R that includes this extracted region Ra (S34), and synthesizes it with the image based on the three-dimensional volume data to control the display device 52 to display (S53).

Thus, as a scanning plan with reference to the previous three-dimensional volume data can be developed, extraction of a tissue image on an image, which is difficult in an X-ray transmission image, becomes possible, and setting of the scanning region becomes simple and accurate. In addition, by referring to the three-dimensional volume data, it is possible to accurately set the tube current at each view angle.

Figure 17:
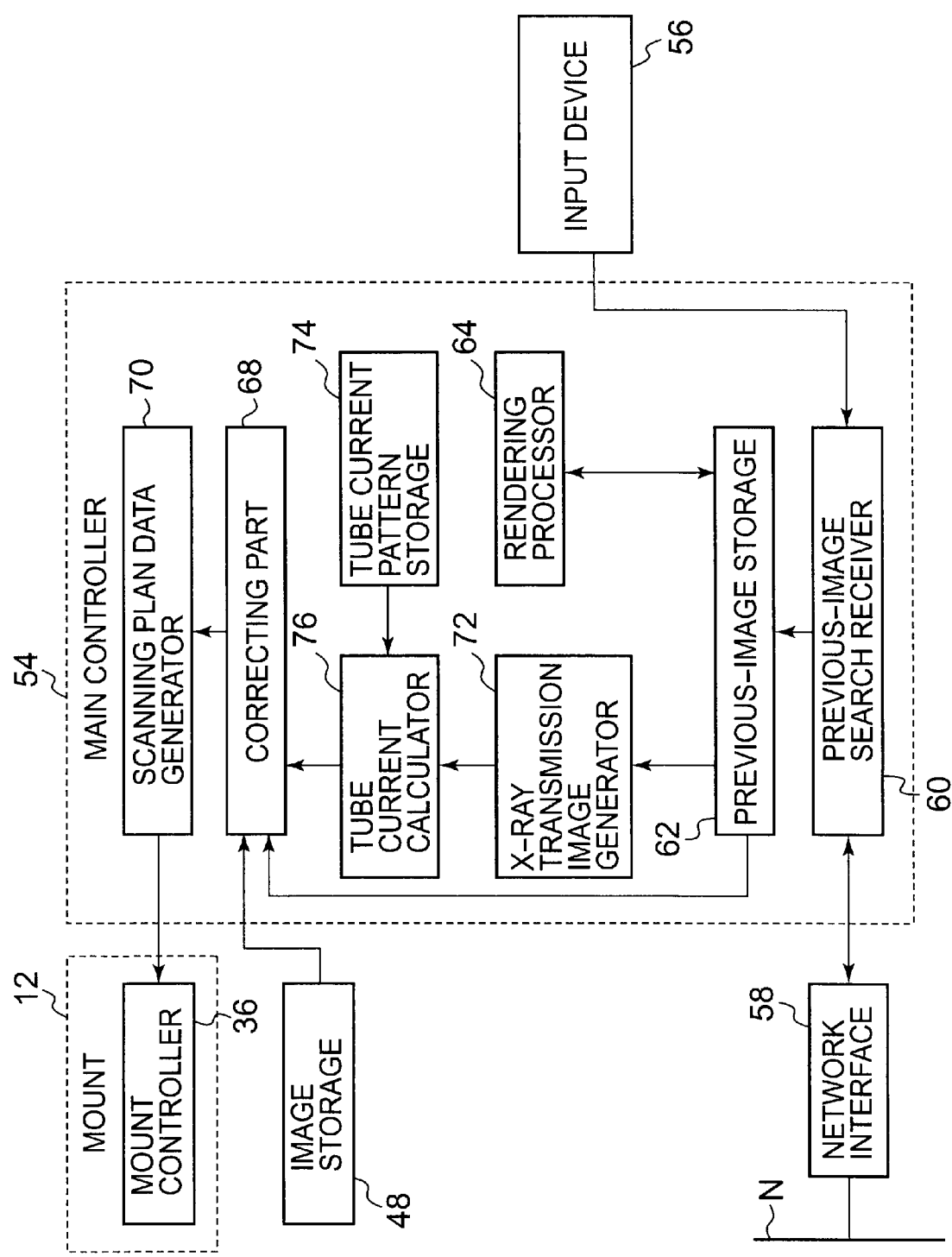
FIG. 17 shows a detailed configuration of the main controller that sets a tube current from the three-dimensional volume data.

FIG. 17 is a block diagram showing a detailed configuration of the main controller 54 configured to set the tube current from the three-dimensional volume data. The same configuration will be provided with the same name and the same reference numeral, and a detailed explanation thereof will be omitted. The main controller 54 further has an X-ray transmission image generator 72, a tube current pattern storage 74, and a tube current calculator 76.

The X-ray transmission image generator 72 generates each X-ray transmission image projected on a plane orthogonal to a line entering from each view angle, on the basis of the three-dimensional volume data. The tube current pattern storage 74 archives information in which the pattern of a pixel value and a tube current value is set for each image SD value. The tube current pattern is acquired beforehand by using, for example, a human body or a human body simulated phantom.

The image SD is a numerical value that represents image noise defining the variation in pixel values of a homogeneous phantom image as display deviation.

The tube current calculator 76 acquires the pixel value of the X-ray transmission image generated by the X-ray transmission image generator 72 and, from the pattern of the pixel value and the tube current value, calculates the tube current supplied by the high-voltage generating device 30 when the X-ray tube 24 is located at the coordinate position (Z, θ) that passes through the pixel with the acquired pixel value, the view angle θ being orthogonal to the X-ray transmission image. Of the coordinate position (Z, θ) of the X-ray tube 24, the coordinate value of the Z-axis corresponds to the coordinate system of the previous three-dimensional volume data.

The correcting part 68 corrects the coordinate position (Z, θ) of the X-ray tube 24 by the amount of displacement Zgap in the Z-axis direction, and sets the calculated tube current as the value when the X-ray tube 24 is located at the coordinate position (Z-Zgap, θ) in the scout image captured this time. The scanning plan data generator 70 generates scanning plan data containing the tube current when the X-ray tube 24 is located at the coordinate position (Z-Zgap, θ), and outputs it to the mount controller 36.

Figure 18:
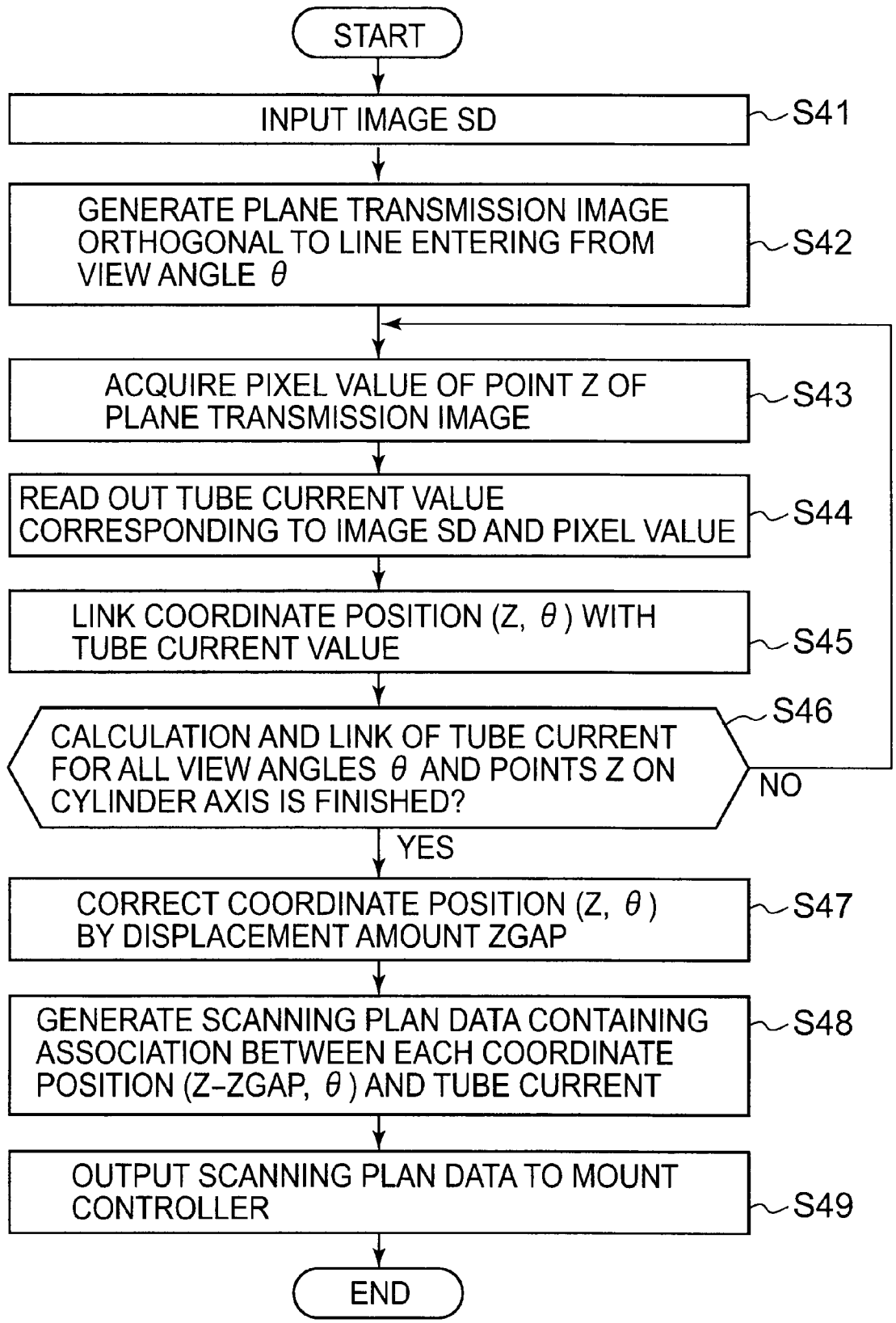
FIG. 18 is a flowchart showing the process of setting the tube current from the three-dimensional volume data.

FIG. 18 is a flowchart showing a process of setting the tube current by using the three-dimensional volume data. First, a pull-down menu for selecting an image SD value is displayed on an input format screen displayed for creating a scanning plan of the display device 52, so an operation of selecting the image SD is previously inputted by the operator using the input device 56 (S41).

Figure 19:
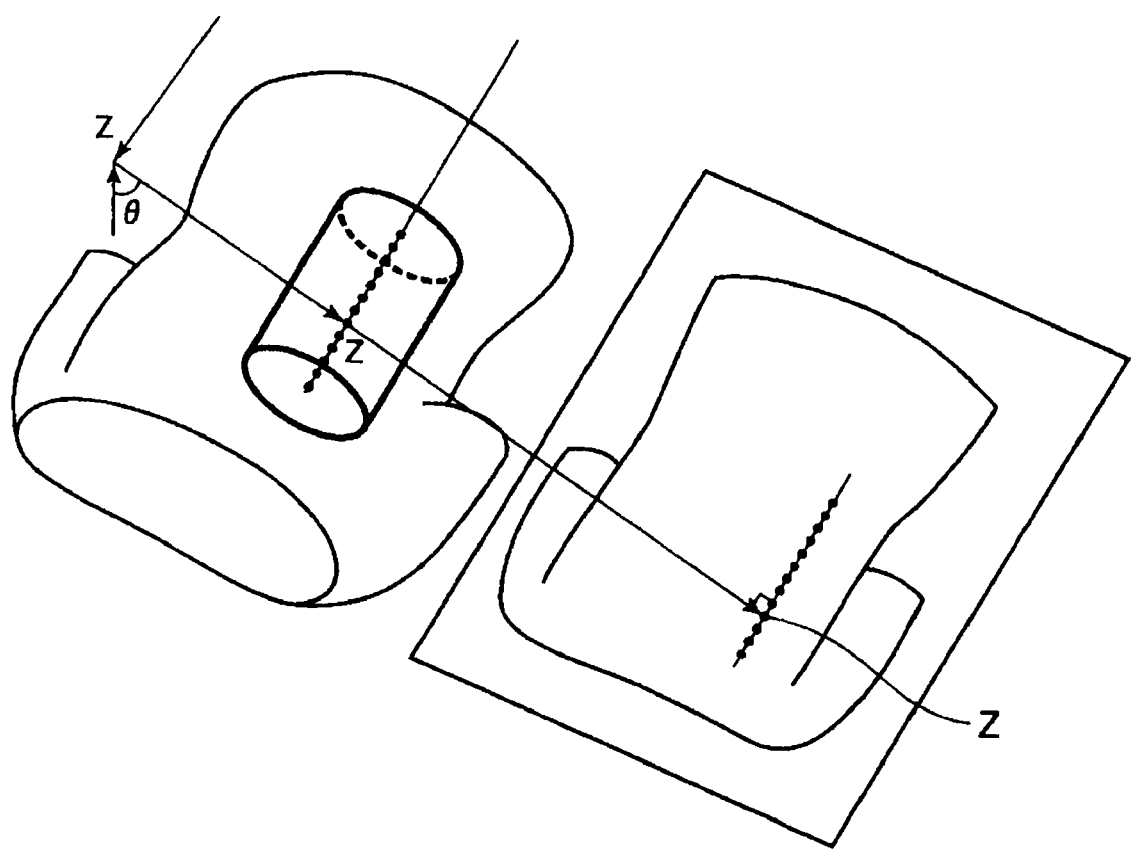
FIG. 19 shows an aspect of projecting the three-dimensional volume data onto a plane orthogonal to a line entering from a view angle θ.

As shown in FIG. 19, the X-ray transmission image generator 72 projects three-dimensional volume data onto a plane orthogonal to a line entering from the view angle θ, thereby generating an X-ray transmission image orthogonal to the line entering from the view angle θ (S42).

Next, the tube current calculator 76 acquires the pixel value of a point Z of the X-ray transmission image (S43). As shown in FIG. 19, the pixel value of the point Z corresponding to a point on a cylinder axis in the scanning region inputted into an image based on the three-dimensional volume is acquired. This point Z is represented by a coordinate Z on the Z-axis corresponding to the point on the cylinder axis in the scanning region. This is because the X-ray is radiated so as to pass through the point on the cylinder axis from the view angle θ.

When the pixel value is acquired, the tube current calculator 76 reads out a tube current value corresponding to the previously selected image SD and the acquired pixel value, from the pattern of the pixel value and the tube current value stored in the tube current pattern storage 74 (S44). When reading out the tube current value, the tube current calculator 76 links the coordinate position (Z, θ) of the X-ray tube 24 with the tube current value having been read out (S45).

The tube current calculator 76 repeats steps S42 to S45 if calculation and link of the tube current is not completed for all view angles θ and each point Z on the cylinder axis (S46, No). If the calculation and link is completed all (S46, Yes), the correcting part 68 corrects each coordinate position (Z, θ) of the X-ray tube 24 with which the tube current is linked by the amount of displacement Zgap, thereby setting it as the coordinate position (Z-Zgap, θ) (S47).

The scanning plan data generator 70 generates scanning plan data containing link of the tube current with each coordinate position having been corrected (Z-Zgap, θ) of the X-ray tube 24 (S48), and outputs it to the mount controller 36 (S49).

Accordingly, by referring to the three-dimensional volume data, it is possible to precisely set a tube current for each view angle that is not orthogonal to a scout image without the need for estimation, whereby it becomes possible to capture a favorable image.

What is claimed is:

1. An X-ray CT system having an X-ray tube that irradiates a subject with an X-ray to capture a cross-sectional image of the subject placed on a bed, the X-ray CT system comprising:
an image storage configured to store a previous image containing previous three-dimensional volume data of the subject;
a capturing part including an X-ray tube irradiating with an X-ray, and a detector configured to capture an X-ray transmission image of the subject;
a measuring part configured to measure an amount of displacement between images of the subject shown in the previous image and the X-ray transmission image;
an inputting part for setting a scanning region;
a display controller configured to control so as to display position mark information representing the scanning region on an image based on the three-dimensional volume data in response to an input to the inputting part; and
a scanning controller configured to control the capturing part to move relative positions of the X-ray tube and the subject by using the amount of displacement to correct the displacement so that the image based on the three-dimensional volume data is captured within the scanning region after the correction, to capture the cross-sectional image.

2. The X-ray CT system according to claim 1, wherein display controller controls so as to display position mark information representing a scanning region on the X-ray transmission image and the image based on the three-dimensional volume data in response to an input to the inputting part, and makes the position of the position mark information on the X-ray transmission image coincide with the position of the position mark information on the image based on the three-dimensional volume by using the amount of the displacement.

3. The X-ray CT system according to claim 1, further comprising:

a CT-value acquiring part configured to acquire a CT value of a designated position within the image based on the three-dimensional volume data in response to an input to the inputting part; and
an extracting part configured to extract a region containing the designated position and having substantially the same value as the acquired CT value,
wherein the display controller controls to display the position mark information with a region including the extracted region as the scanning region.

4. The X-ray CT system according to claim 1, further comprising:
a tube current calculator configured to calculate a tube current at each capturing position on the basis of an inputted image SD value and the three-dimensional volume data, and link the each position with the tube current; and
a correcting part configured to correct the linked position by the amount of displacement, wherein
the image SD is a numerical value that represents image noise defining a variation in pixel values of a homogeneous phantom image as display deviation, and
when the X-ray tube reaches the corrected position, a tube current linked with the corrected position is applied to the X-ray tube.

5. The X-ray CT system according to claim 4, wherein the tube current calculator includes:
an X-ray transmission image generator configured to project the three-dimensional volume data from each view angle and generate an X-ray transmission image orthogonal to the view angle; and
a calculator configured to calculate, from the inputted image SD value and a pixel value of a single point on the X-ray transmission image generated by the X-ray transmission image generator, the tube current at the position through the single point and with the view angle.

6. The X-ray CT system according to claim 1, wherein the measuring part uses a previous X-ray transmission image captured in pre-scan performed before capture for acquiring the three-dimensional volume data as the previous image, thereby measuring the amount of displacement from the previous image and the X-ray transmission image.

7. The X-ray CT system according to claim 6, wherein the measuring part calculates the amount of displacement in each direction of three dimensions on the basis of two types of previous images and two types of X-ray transmission images captured from two orthogonal directions.

8. The X-ray CT system according to claim 1, further comprising:
a three-dimensional image generator configured to, when the image based on the previous three-dimensional volume data of the subject is not stored in the image storage, generate the image from the three-dimensional volume data.

9. The X-ray CT system according to claim 1, wherein the display controller controls to display the position mark information representing the scanning region on a three-dimensional image, as the image based on the three-dimensional volume data.

10. The X-ray CT system according to claim 1, wherein
the inputting part sets a three-dimensional scanning area, and
the scanning controller is further configured to control the capturing part to capture a three-dimensional image including the three-dimensional scanning area.

11. A method for creating a scanning plan for an X-ray CT system having a capturing part that includes an X-ray tube irradiating a subject with an X-ray and a detector configured to capture a cross-sectional image of the subject placed on a bed, and an inputting part for setting a scanning region of the subject, the scanning plan creating method comprising:

storing a previous image containing previous three-dimensional volume data of the subject;

capturing an X-ray transmission image of the subject by the capturing part;

measuring the amount of displacement in image of the subject shown in the previous image and the X-ray transmission image;

displaying position mark information showing the scanning region in response to an input to the inputting part, on an image based on the three-dimensional volume data; and moving relative positions of the X-ray tube and the subject by using the amount of displacement to correct the displacement so that the image based on the three-dimensional volume data is captured within the scanning region after the correction, and to capture the cross-sectional image.

12. The scanning plan creating method according to claim 11, wherein, in the displaying of the position mark information, in response to an input to the inputting part, a display position of position mark information representing a scanning region on the X-ray transmission image and the position mark information on the image based on the three-dimensional volume data are displayed together by using the amount of displacement, on the X-ray transmission image and the image based on the three-dimensional volume data.

13. The scanning plan creating method according to claim 11, wherein, in the displaying of the position mark information representing the scanning region in response to the input to the inputting part:

a CT value of a designated position within the image based on the three-dimensional volume data in response to an input to the inputting part is acquired;

a region containing the designated position and having substantially the same value as the acquired CT value is extracted; and a region including the extracted region is displayed as the position mark information representing the scanning region.

14. The scanning plan creating method according to claim 11, wherein:

a tube current at each capturing position is calculated based on an inputted image SD value and the three-dimensional volume data, and the each position is linked with the tube current;

the image SD is a numerical value that represents image noise defining a variation in pixel values of a homogenous phantom image as display deviation;

the linked position is corrected by the amount of displacement; and when the X-ray tube reaches the corrected position, a tube current linked with the corrected position is applied to the X-ray tube.

15. The scanning plan creating method according to claim 11, wherein, in the measuring of the amount of displacement, a previous X-ray transmission image captured in pre-scan performed before capture for acquiring the three-dimensional volume data is used as the previous image, and the amount of displacement is measured from the previous image and the X-ray transmission image.

16. The scanning plan creating method according to claim 15, wherein the amount of displacement in each direction of three dimensions is calculated on the basis of two types of the previous images and two types of the X-ray transmission images captured from two orthogonal directions.

17. The scanning plan creating method according to claim 11, wherein the position mark information representing the scanning region is displayed on a three-dimensional image as the image based on the previous three-dimensional volume data of the subject.

* * * * *